US006521263B1

United States Patent
Pritchard et al.

(10) Patent No.: US 6,521,263 B1
(45) Date of Patent: Feb. 18, 2003

(54) IMMUNOMODULATORY FACTORS FOR IMMUNOSUPPRESANT AND ANTIALLERGIC TREATMENT

(75) Inventors: David Idris Pritchard, Nottingham (GB); Paul Williams, Nottingham (GB)

(73) Assignee: University of Nottingham (GB)

( * ) Notice: Subject to any disclaimer, the term of this patent is extended or adjusted under 35 U.S.C. 154(b) by 0 days.

(21) Appl. No.: 09/830,738

(22) PCT Filed: Nov. 2, 1999

(86) PCT No.: PCT/GB99/03621

§ 371 (c)(1),
(2), (4) Date: Jun. 25, 2001

(87) PCT Pub. No.: WO00/25810

PCT Pub. Date: May 11, 2000

(30) Foreign Application Priority Data

Nov. 3, 1998 (GB) .............................................. 9824034

(51) Int. Cl.⁷ ............................................... A61K 35/56
(52) U.S. Cl. ...................................................... 424/520
(58) Field of Search .......................................... 424/520

(56) References Cited

FOREIGN PATENT DOCUMENTS

| WO | 9629082 | 3/1996 |
|----|---------|--------|
| WO | 9933479 | 12/1998 |

OTHER PUBLICATIONS

Monroy, Fernando, Colin Dobson and John H. Adams (1989) "Low Molecular Weight Immunosuppressors Secreted by Adult *Nematospiroides dubius*" *International Journal of Parasitology*19(1):125–128.

Pritchard, D.I., C.E. Lawrence, P. Appleby, I.A. Gibb, and K. Glover (1994) "Immunosuppressive Proteins Secreted By The Gastrointestinal Nematode Parasite *Heligmosomoides polygyrus*" *Int. J. Parasitol.* 24(4):495–500.

Telford, G., d.J. Wheeler, P. Appleby, I.G. bowen, D.I. Pritchard (Dec. 1998) "*Heligmosomoides polygyrus* immumomodulatory factor (IMF), targets T–lymphocytes" *Parasite Immunology* 20(12):601–611.

Primary Examiner—Jean C. Witz
(74) Attorney, Agent, or Firm—Saliwanchik, Lloyd & Saliwanchik

(57) ABSTRACT

An immunosuppressive agent, obtainable from the nematode *Heligmosomoides polygyrus*, characterised in that the agent has a molecular weight of less than 12 kDa, is resistant to proteinase K and is not bound to a polypeptide.

11 Claims, 4 Drawing Sheets

IMMUNOMODULATORY FACTORS FOR IMMUNOSUPPRESANT AND ANTIALLERGIC TREATMENT

FIELD OF THE INVENTION

This invention relates to immunomodulatory factors for use in immnunosuppressant and antiallergic treatment.

BACKGROUND OF THE INVENTION

Allergic rhinitis (e.g. hayfever) and asthma are typical results of the immune system response to inhaled molecules such as allergens and antigens. It has been established that the cross-linking of antibodies initiates a series of biochemical and pharmological events including the release of potent mediators of inflammation, which results in allergic reactions, including: difficulty in breathing; itching; excess mucous secretion etc; up to and including life-threatening allergic reactions in some rare situations.

Therapeutically, many agents are used to try to prevent the release of mediators and/or to treat the downstream events by blocking or reducing the effects of the mediators on target tissues. None of the currently available treatments are ideal, and each has problems such as side effects and breakthroughs.

Immunosuppressant compounds induce an inhibition of the immune response system. The immune mediated rejection process is the major cause of graft loss in organ transplantation. Dramatic improvements in immunosuppression and subsequent organ graft and patient survival have been obtained using immunosuppressive compounds.

Autoimmune diseases are disorders where the host discrimination of "self" versus "non-self" breaks down and the individual's immune system (both acquired and innate components) attacks self tissues. Indications are that the main and fundamental error responsible for the induction and persistence of most autoimmune diseases resides within auto-reactive proliferating T lymphocytes.

The currently available immunosuppressant drugs have the disadvantage of a narrow therapeutic range. The compounds are known to be nephrotoxic, neurotoxic and potentially diabetogenic and, therefore are of limited use. Problems also exist with the administration of these compounds, their bioavailability and the monitoring of their levels both clinically and in the laboratory.

The murine trichostrongyle nematode *Heligmesomoides polygyrus* resists the immune system and resides in the mouse duodenum for eight months or more during primary infection. Where immunity is generated against this parasite in artificial experimental situations, it appears to be mediated by Th2 cells and their associated cytokines. However, the parasite has seemingly evolved mechanisms to counteract a potentially protective Th2 response, given the chronicity of natural infections. Simultaneously, infection with *Heligmosomoides polygyrus* suppresses immune responses to a variety of heterologous antigens such as ovine erythrocytes and other nematode parasites normally expelled by what we now know to be Th2 mediated immune mechanisms. Suppressive activity is also demonstrable in vivo, and in vitro using parasite extracts or excretory secretory (ES) products (Pritchard el al, Immunology (1984); 51:633–642 and Pritchard et al, Int. J. Para. (1994); 24:495–500).

SUMMARY OF THE INVENTION

The present invention is based on the isolation of an immunomodulatory factor (IMF) from the nematode *Heligmosomoides polygyrus* which acts to interfere with T cell function, possibly by increasing the production of $CD8^+$ T cells with a simultaneous decrease in $CD4^+$ T cells. Therefore, according to the present invention, an immunosuppressive agent is disclosed, wherein the agent is obtainable from the nematode *Heligmosomoides polygyrus* and is characterised by having a molecular weight of less than 12 kDa and being substantially free of bound polypeptides. The agent may be non-proteinaceous.

The agent may be used in the manufacture of a medicament for the treatment of allergic or autoimmune disorders. In particular, the agent may be used in the manufacture of a medicament for the prevention of graft rejection during organ or tissue transplantation. The agent may also be used in the treatment of other autoimmune disorders, for example rheumatoid arthritis and multiple sclerosis.

DESCRIPTION OF THE INVENTION

Figure 1:
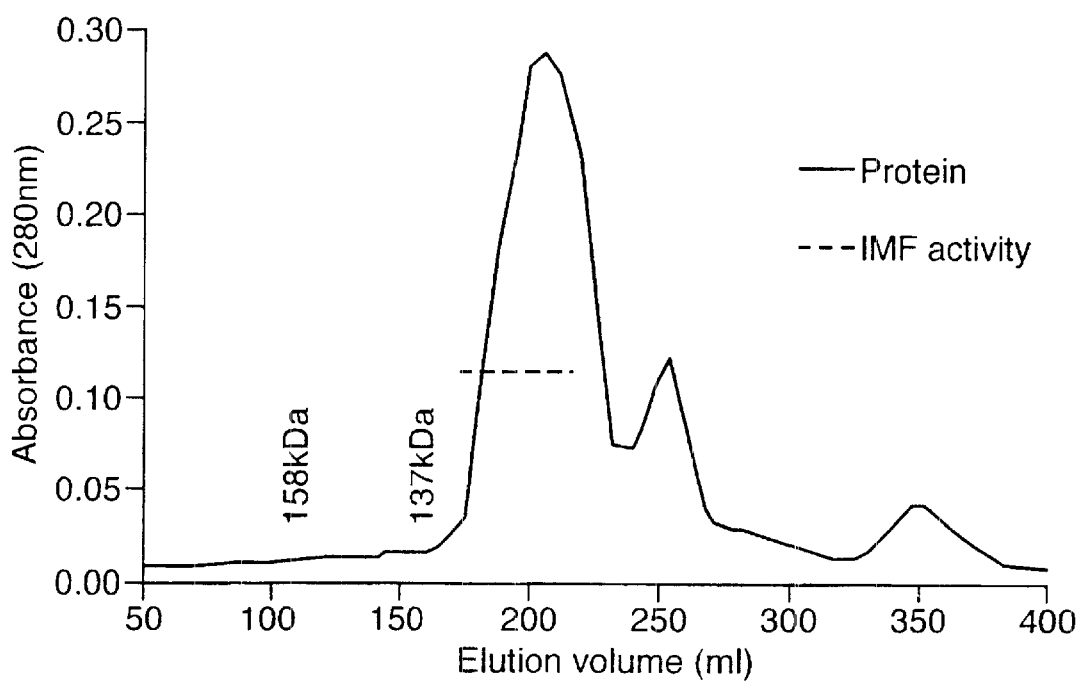
FIG. 1a illustrates the elution profile of active immunosuppressive agent (IMF) during gel filtration chromatography using Sephacryl S-200SF.

The agents of the present invention may be obtained from the nematode *Heligmosomoides polygyrus*. The agents act to reduce the Th2-mediated immune response. While not wishing to be bound by theory, the activity of the agents may be due to a stimulation of the production of $CD8^+$ cells and simultaneous reduction in $CD4^+$cells. $CD8^+$ cells have been implicated in the suppression of IgE production, possibly through the production or induction of interferon-$\gamma$.

The invention will now be further illustrated by way of example only, with reference to the accompanying drawings.
Infection of Animals and Recovery of Worms.

CFLP mice, bred in-house, were infected orally with $400 l_3$ larvae of *H. polygyrus* and kept on a 12 h light/dark cycle. Adult worms were recovered ten days later using a modified Baermann technique (Pritchard et al, 1994, supra).
Collection of Excretory/secretory (ES) Products.

Adult *H. polygyrus* were sanitised by washing for 4 h in several changes of sterile saline (0.9% w/v NaCl) containing 100 U/ml penicillin and 100 $\mu$g/ml streptomycin. They were transferred to Hanks' balanced salt solution and cultured for 24 h at 37° C. The resultant ES products were filter sterilised using a 0.22 $\mu$m filter and stored frozen at −20° C. Protein concentrations were estimated using the Lowry assay.

Fractionation of ES Products.

The immunosuppressive agent (IMF) does not survive in an active state during ion-exchange chromatography, therefore ES products were fractionated on a Sephacryl S-200SF (Pharmacia Biotech) column equilibrated with 100 mM ammonium acetate isocratic elution profile. 5 ml fractions were collected, freeze dried, and redissolved in 1 ml sterile phosphate buffered saline (PBS), then tested for immunosuppressive activity using the murine keyhole limpet haemocyanin antibody production (KAP) assay (Pritchard et al, 1994, supra) and protein content using the Lowry method assay. Active fractions were pooled, labelled as IMF and stored frozen.

Keyhole Limpet Haemocyanin (KLH) Antibody Production (KAP) Assay for the Detection of Immunomodulatory Activity.

The KAP assay is driven by lymphocytes, which produce high levels of interleukin-4 (IL-4) after stimulation by antigen-presenting B lymphocytes and is therefore a good in vitro model of the Th2 driven immune response. 100 $\mu$l spleen cells from animals primed with KLH in vivo ($2.5 \times 10^7$ cells/ml in RPMI 1640+10% foetal calf serum (FCS)+L-glutamine+2-mercaptoethanol+penicillin+streptomycin), 50 $\mu$l test material and 100 $\mu$l KLH at 16.7 $\mu$g/ml were cultured at 37° C. for 6 days in 5% $CO_2$/air.

The cells were washed by centrifugation at 300×g in a Centra 7R centrifuge and by removing and replacing 175 $\mu$l of medium, the process being repeated twice. After a further 24 h of incubation, the supernatants were harvested and replicates pooled and stored frozen at −20° C. Samples were later assayed for anti-KLH antibodies by ELISA. Microtitre 96-well plates were coated overnight at 4° C. with 150 $\mu$l KLH at 10 $\mu$g/ml in 50 mM carbonate/bicarbonate buffer, pH9.6. The plates were washed three times with phosphate buffered saline, pH7.2, containing 0.05% Tween-20 (PBS/tween). 150 $\mu$l of samples, diluted 1 in 4 in PBS/tween, were added and incubated for 2 h at room temperature (RT). After plate washing, 150 $\mu$l anti-mouse IgG (whole molecule) alkaline phosphatase conjugate, at 1 in 500 in PBS/tween, was added and incubated at RT for 2 h. The plates were washed and 150 $\mu$l p-nitrophenyl phosphate at 1 mg/ml in 50 mM carbonate buffer pH9.8+1 mM $MgCl_2$ added. After 30 mins colour development, optical density was measured on a plate reader at a wavelength of 405 nm. To investigate the proteinaceous properties of IMF, ES was treated with immobilised proteinase-K (500 $\mu$l ES+100 $\mu$l proteinase-K agarose as a slurry in PBS, for 2 h at 37° C.). As controls, agarose or heat treated proteinase-K agarose (100° C., 5 min) was substituted.

Production of Immunomodulatory Factor (IMF) from ES Products.

The fractionation of ES product by gel filtration on Sephacryl S-200SF produced one IMF containing peak as indicated by activity in the KAP assay. The trace is represented in FIG. 1. Calibration of the column with protein standards of known molecular weights indicated activity to be associated with material of a size less than 12 kDa. Lower molecular weight standards all co-eluted with the IMT fraction. SDS-PAGE also indicated material of a mass <12 kDa.

Suppression of Antibody Production by IMF.

Figure 2:
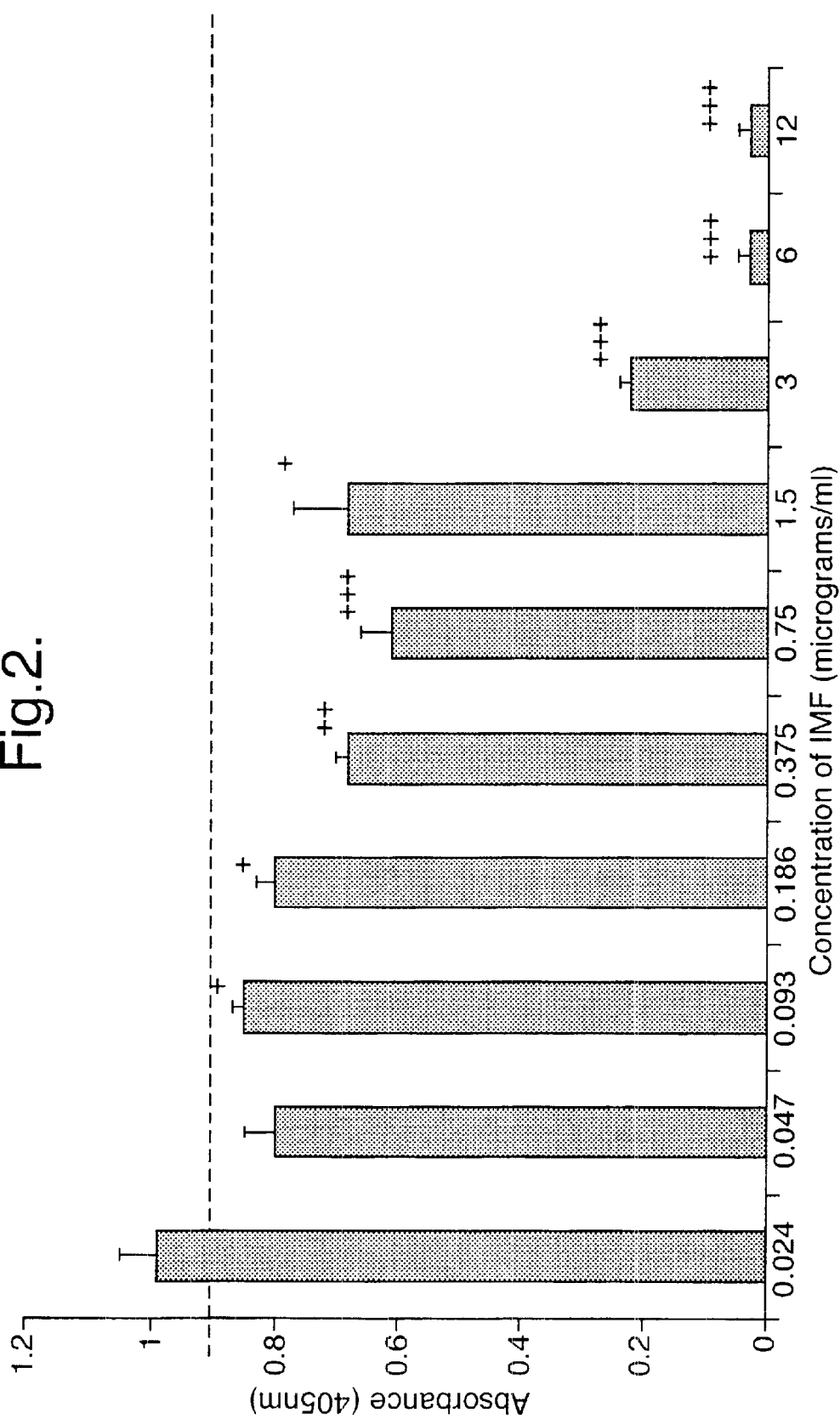
FIG. 2 illustrates the effect of the immunosuppressive agent on anti-KLH antibody production in the KAP assay.
Figure 3:
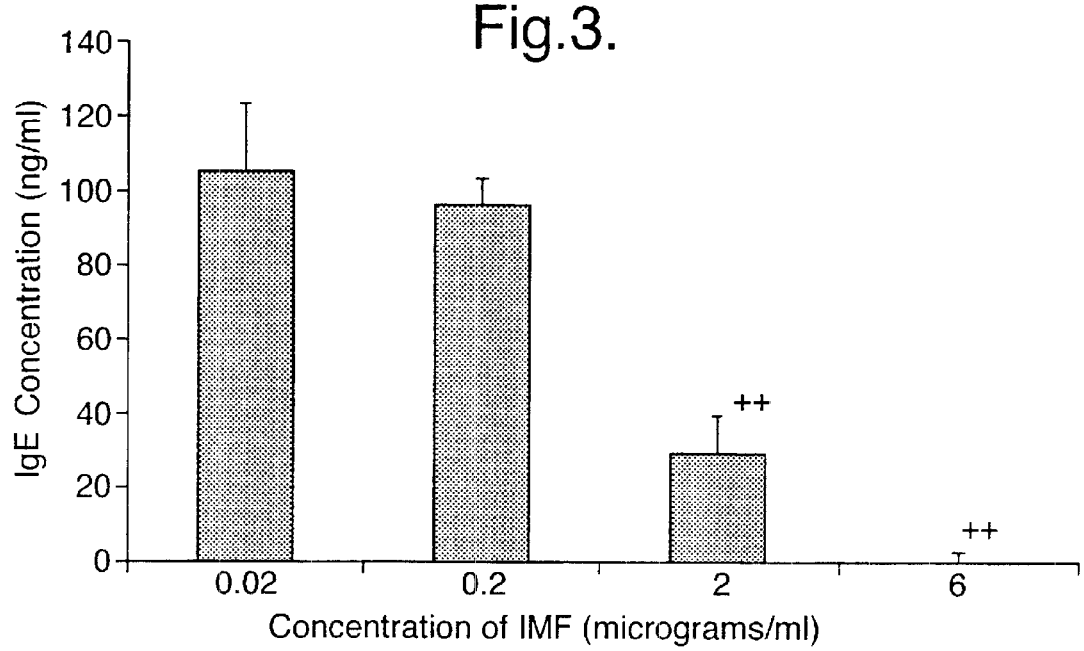
FIG. 3 illustrates the effect of the agent on IgE production.
Figure 4:
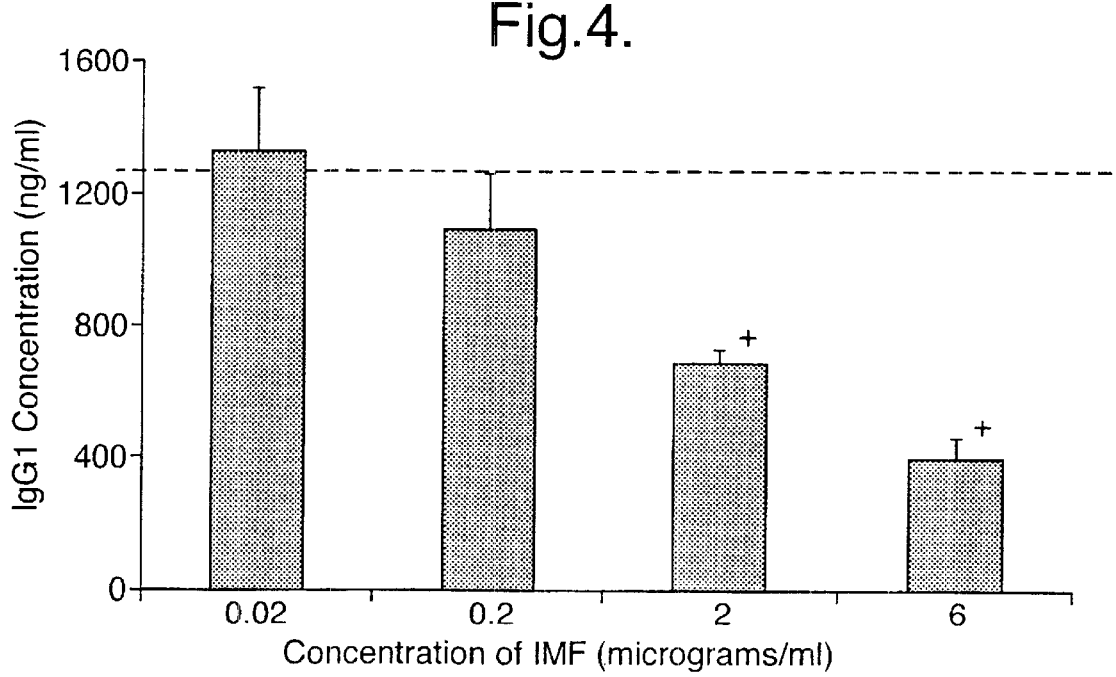
FIG. 4 illustrates the effect of the agent on IgG1 production.
Figure 5:
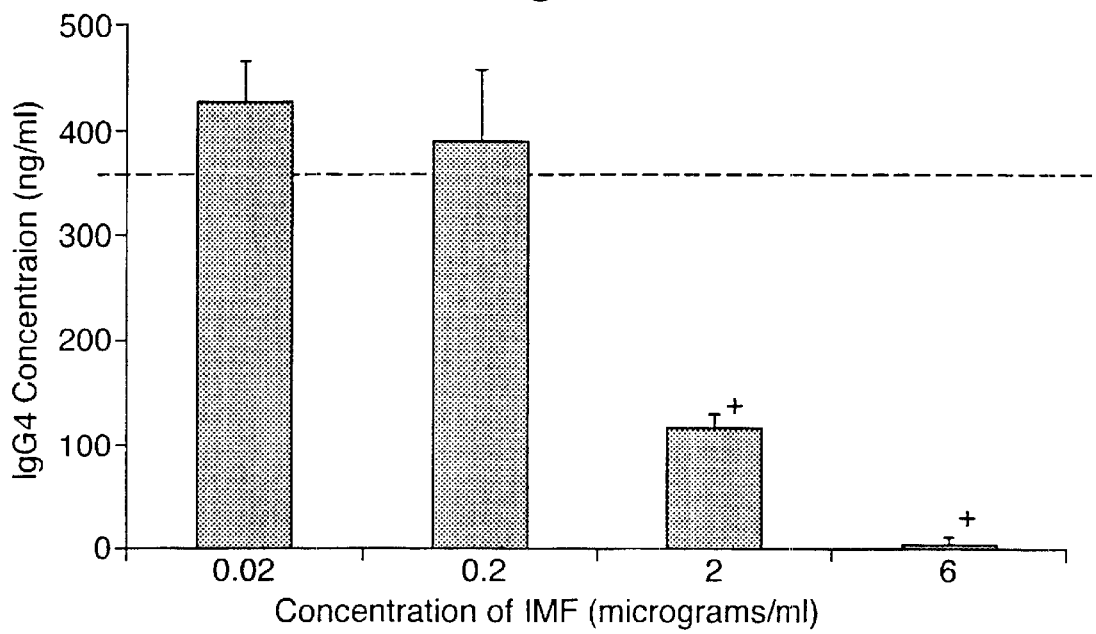
FIG. 5 illustrates the effect of the agent on IgG4 production.

FIG. 2 shows that IMF produced a dose-dependent suppression of specific anti-KLH antibody production in the KAP assay. Substantial biological activity was noted at an IMF concentration of 0.75 $\mu$g/ml (p<0.001) and significant suppression was still present at 0.093 $\mu$g/ml (p<0.05). In addition, it was shown that IMF inhibited IgE production by IL-4 stimulated Proliferating Blood Mononucleocytes (PBMC) at 2 $\mu$g/ml (p<0.01) (FIG. 3). IMF also significantly inhibited the production of IgG1 and IgG4 by human PBMC in vitro. Significant inhibition occurred to 2 $\mu$g/ml (p<0.05), for both isotypes, as shown in FIG. 4 and FIG. 5 respectively.

Site of Action Studies:—IMF Requires the Presence of T-lymphocytes to Exert its Effects on Antibody Production.

IMF-induced suppression of IgE production was not demonstrable in an IL-4/CD40 stimulated T cell-depleted IgE culture system.

Figure 6:
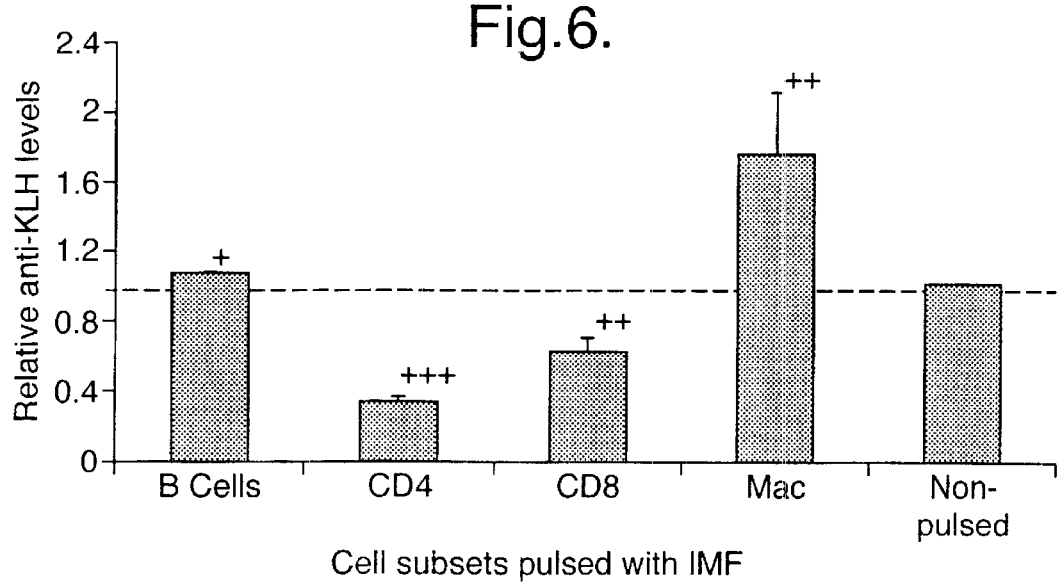
FIG. 6 illustrates the effect of the agent on different murine cell subsets.

The effect of prepulsing different murine cell subsets with ES products is shown in FIG. 6. The specific antibody levels, expressed as amounts relative to that produced by the non-pulsed cells, show that prepulsing of both T-lymphocyte subsets ($CD4^+$ and $CD8^+$) caused a significant reduction in antibody production, the greater reduction being associated with the $CD4^+$ subset (−70%, p<0.001). Prepulsing of B-lymphocytes had an insignificant effect on antibody production, whereas prepulsing of the adherent cell population brought about an increase in antibody production (+70%, p<0.01).

Flow cytometric analysis of cultured murine cells from the KAP assay is shown in Table 1.

TABLE 1

| Treatment | CD4 | CD8 | LY5 | CD4/8 ratio |
|---|---|---|---|---|
| IMF | 501 ± 47 | 222 ± 26 | 381 ± 43 | 2.3 |
| PBS | 408 ± 36 | 84 ± 20 | 245 ± 57 | 4.9 | and indicates a significant increase in the absolute numbers of $CD8^+$ T cells, after a period of only 24 h in culture.

Treating the ES fractions with proteinase K had no effect on the inhibitory activity of the agent and shows that the agent may not be a protein.

The agent may be further purified by techniques known in the art. In particular, antibody based purification techniques and gel electrophoresis may be used.

It will also be appreciated by the skilled person that the purified agent may be formulated in a known way to provide a therapeutic, particularly to treat an autoimmune disorder e.g. asthma, arthritis or allergic rhinitis. Suitable formulations can be developed for oral or systemic delivery. Suitable excipients, diluents and delivery agents will be apparent to the skilled person from conventional formulation techniques.

I claim:

1. An immunosuppressive agent, obtainable from the nematode *Heligmosomoides polygyrus*, characterized in that the agent has a molecular weight of less than 12 kDa, is resistant to proteinase K and is not bound to a polypeptide.

2. The agent, according to claim 1, wherein said agent is non-proteinaceious.

3. A method for providing immunosuppresant or antiallergic treatment to a patient in need of such treatment wherein said method comprises administering to the patient an effective amount of an agent having immunosuppressive or antiallergic activity, wherein said agent has a molecular weight of less than 12 kDa, is resistant to proteinase K and is not bound to a polypeptide.

4. The method, according to claim 3, wherein said treatment is for treating an autoimmune disorder.

5. The method, according to claim 4, wherein said disorder is selected from the group consisting of asthma, allergic rhinitis, and rheumatoid arthritis.

6. The method, according to claim 3, wherein said treatment is for the prevention of graft or tissue rejection.

7. The method, according to claim 3, wherein said agent is non-proteinaceious.

8. The method, according to claim 3, wherein said agent is administered orally.

9. A pharmaceutical composition comprising an immunosuppressive agent, obtainable from the nematode *Heligmosomoides polygyrus*, characterized in that the agent has a molecular weight of less than 12 kDa, is resistant to proteinase K and is not bound to a polypeptide; wherein said composition further comprises a pharmaceutical carrier.

10. The composition, according to claim 9, wherein said agent is non-proteinaceious.

11. The composition, according to claim 9, Which is adapted for oral administration.

* * * * *

UNITED STATES PATENT AND TRADEMARK OFFICE
CERTIFICATE OF CORRECTION

PATENT NO.     : 6,521,263 B1
DATED          : February 18, 2003
INVENTOR(S)    : David Idris Pritchard and Paul Williams It is certified that error appears in the above-identified patent and that said Letters Patent is hereby corrected as shown below:

<u>Column 1,</u>
Line 51, "Heligmesomoides" should be -- Heligmosomoides --.

<u>Column 6,</u>
Line 10, "Which" should be -- which --.

Signed and Sealed this

Sixteenth Day of September, 2003

JAMES E. ROGAN
*Director of the United States Patent and Trademark Office*